(12) United States Patent
Sharma et al.

(10) Patent No.: US 6,656,118 B2
(45) Date of Patent: Dec. 2, 2003

(54) METHOD AND APPARATUS FOR DATA MINING OF AN ULTRASOUND SCANNER

(75) Inventors: Sanjeev Sharma, Waukesha, WI (US); Hui Ann Liew, Evanston, IL (US)

(73) Assignee: GE Medical Systems Global Technology Company LLC, Waukesha, WI (US)

(*) Notice: Subject to any disclaimer, the term of this patent is extended or adjusted under 35 U.S.C. 154(b) by 0 days.

(21) Appl. No.: 09/683,330

(22) Filed: Dec. 14, 2001

(65) Prior Publication Data

US 2003/0114753 A1 Jun. 19, 2003

(51) Int. Cl.[7] ............................................. A61B 8/00
(52) U.S. Cl. ....................................... 600/437; 709/217
(58) Field of Search ................................... 600/437, 443, 600/447; 705/2–3; 707/10, 104.1; 709/206, 217–219

(56) References Cited

U.S. PATENT DOCUMENTS

| | | | |
|---|---|---|---|
| 5,715,823 A | | 2/1998 | Wood et al. |
| 5,851,186 A | | 12/1998 | Wood et al. |
| 5,891,035 A | | 4/1999 | Wood et al. |
| 6,224,551 B1 | | 5/2001 | Mullen |
| 6,272,469 B1 | | 8/2001 | Koritzinsky |
| 6,353,445 B1 | * | 3/2002 | Babula et al. ............... 345/733 |
| 6,377,162 B1 | * | 4/2002 | Delestienne et al. ... 340/286.07 |
| 6,381,557 B1 | * | 4/2002 | Babula et al. ............... 702/183 |
| 6,424,996 B1 | * | 7/2002 | Killcommons et al. ..... 709/206 |
| 6,434,572 B2 | * | 8/2002 | Derzay et al. ........... 707/104.1 |

OTHER PUBLICATIONS

2002/0067798 A1 6–6–02 Lang, Philip 378/54.*

* cited by examiner

Primary Examiner—Francis J. Jaworski
(74) Attorney, Agent, or Firm—McAndrews, Held & Malloy, Ltd.; Peter J. Vogel; Michael A. Dellapenna

(57) ABSTRACT

A method and apparatus are disclosed for monitoring multiple ultrasound scanners of differing platform types for system events, acquiring system event data of the ultrasound scanners, and transferring the system event data to a remote location by applying a common data mining module and log viewer component in each scanner to act as an interface between a web server and control processing section within the scanners. A computer at an automated support center that is remote to the scanners interfaces to the web servers of the scanners over a network. The remote computer has a web browser to survey the scanners by communicating with the web servers over the network. The data mining module continuously monitors the scanners for system events. Log files are generated within the scanners during normal operation of the scanner. The log viewer component translates system event log files within the scanners in response to internal requests occurring in the scanners at regular, predefined time intervals. The system event information is displayed to an operator at the automated support center and/or formatted to provide to a customer for each scanner.

32 Claims, 2 Drawing Sheets

METHOD AND APPARATUS FOR DATA MINING OF AN ULTRASOUND SCANNER

BACKGROUND OF INVENTION

Certain embodiments of the present invention relate to a medical diagnostic ultrasound scanner. More particularly, certain embodiments relate to a method and apparatus for monitoring system event data within an ultrasound scanner and acquiring the system event data at a remote location using programs that provide cross-platform/server interoperability.

Ultrasound scanners to detect faults, problems, and general status within the scanner are well established. Ultrasound scanners typically comprise different hardware and software implementations that perform various operations such as scan data collection and scan data conversion. There are different software diagnostic tests that perform routine troubleshooting of the hardware assemblies. Other tests provide data on software functioning and general scanner status by logging the data in files. The diagnostic software tests are resident on the scanner and may be operated by a person having direct access to the console of the scanner. However, the tests are not always accessible remotely, that is, from a remote computer through a connection to, for example, a network through a modem. Also, system event data such as probe usage and exam start and end times are not collected.

Other scanners provide remote access through, for example, a VT-100 based remote interface or a common gateway interface (CGI) used for performing various remote services. The interfaces are dependent on specific software and hardware configurations and are not always optimized in terms of performance as the software platform is changed or upgraded. To improve the performance, a new interface that is consistent with the latest software platform would have to be designed.

Also, system event data is not captured and made available over a network to a remote location in the prior art. System events include exam start and end times, active mode time, active probes used during an exam, calculations made during an exam, and other events. System event data may be used to assess various productivity aspects and ultrasound usage.

For example, a method described in U.S. Pat. No. 5,715,823 to Wood et al. describes using common gateway interface (CGI) programs to access ultrasound images and diagnostic data. A method described in U.S. Pat. No. 5,891,035 to Wood et al. describes accessing images and information from internal and external databases by means of a browser within an ultrasound system and connecting the browser to a network. A method described in U.S. Pat. No. 5,851,186 to Wood et al. describes electronically acquiring a diagnostic ultrasound image over a communications network such that an ultrasound system has a server. A method described in U.S. Pat. No. 6,224,551 B1 to Mullen describes storing ultrasound image data in a database storage device and using an internet protocol. A method described in U.S. Pat. No. 6,272,469 B1 to Koritzinksy et al. describes downloading operational protocols to diagnostic machines from a remote location over a network.

The well-established Internet enables computers at one location to communicate with computers at other locations. The technique of packet switching is typically used to transfer data from one computer to another over the Internet. Information from one user of a network is sent to another user of the network by breaking the information up into discrete units of digital information called packets. Packets of information are transferred across the network by high-speed routers that seek out a network route from one point to another in the network. At a destination point in the network, packets are received and reassembled to re-institute the originally sent message of information.

Transferring information via packets allows a network to accommodate many messages at a time by interleaving packets originating from different locations. Many computers may operate on a network at the same time and may transfer information quickly across the network in the form of packets. The higher cost of a dedicated communication path is avoided. However, as the number of users of the network increase, the larger number of messages being sent may result in a longer amount of time being required to transfer all of the packets in any given message over the network to its destination. But enhancements in computer technology and performance over time allow higher volumes of information to be transferred across a network at faster rates.

The Internet comprises multiple networks that allows for the transfer of information among many users who are linked into the network. To facilitate the transfer of information across the Internet, the World Wide Web (WWW) was created to be used as a high-level user interface to the Internet. A distributed menu system is provided by the WWW where menu pages are displayed such that a user may request information from another system on the Internet. The WWW provides the ability for a user to hop from one web site of information to another by way of displayed hypertext links. A hypertext link allows a user to click on a hypertext component, transferring to a web page associated with that hypertext component, regardless of where the web page is actually located or hosted. A user may download information from the web page and/or go on to another or previous web page in a similar manner. By employing hypertext linking, a user may rapidly link to the desired information on the WWW for which he is searching. Information received from a given web site may be formatted as text, images, graphics, video, and audio.

By incorporating a standard server into an ultrasound machine, the power of the Internet may be employed to access system event data generated by the ultrasound scanner. Accessing system event data as described herein has not been previously accomplished in ultrasound scanners.

A need exists to monitor and acquire system event data of ultrasound scanners, transfer the data to a remotely located support center, and format the system event data such that the system event data may be displayed to an operator and/or provided to a customer. A need also exists for the monitoring and acquisition components to provide cross-platform/server interoperability such that they may be used on multi-generational products.

SUMMARY OF THE INVENTION

An embodiment of the present invention provides for monitoring system events in multiple ultrasound scanners of differing platform types, acquiring system event data of the ultrasound scanners, and transferring the system event data to a remote location by applying a data mining module and log viewer component in each scanner acting as an interface between a control section of the scanners and a web server within the scanners. The data mining module and log viewer component provide cross-platform/server interoperability and may be used on multi-generational products. As used herein, cross-platform/server interoperability means capable of being interfaced to scanners having different operating system and hardware on which the programs are being run. The system event data is transferred to a remote location over a network by communicating with the web servers of the ultrasound scanners over the network. The data mining module monitors system events within the scanners during normal operation of the scanners and generates system event data stored in log files. The log viewer component translates the system event data in the log files to the web servers and the web servers transfer the information to the remote location over the network at regular, pre-defined time intervals. The system event data is formatted such that the system event data may be displayed to an operator and/or provided to a customer for each scanner.

Apparatus is provided for monitoring system events of multiple ultrasound scanners of differing platform types, acquiring system event data from the scanners, and transferring the system event data to a remote location by employing a log viewer component and data mining module in each scanner acting as an interface between a control processing module within the scanners and a web server within the scanners. The log viewer component and data mining module provide cross-platform/server interoperability and may be used on multi-generational products. An automated support center that is remote to the scanners interfaces to the web servers of the scanners over a network. A remote computer within the automated support center has a web browser to communicate with the web servers within the scanners over the network. The data mining module within each scanner monitors the scanners for system events and records system event data in log files within the scanners. The log viewer translates the system event data in the log files to the web servers and the web servers transfer the system event data to the automated support center over the network at regular, pre-defined time intervals. The system event data is formatted such that the system event data may be displayed to an operator and/or provided to a customer for each scanner.

A method is also provided to monitor system events in multiple ultrasound scanners of differing platform types, acquire system event data of the ultrasound scanners, and transfer the system event data to a remote location by applying a data mining module and log viewer component in each scanner acting as an interface between the control processing within the scanners and a web server within the scanners. The data mining module and log viewer component provide cross-platform/server interoperability and may be used on multi-generational products. The web servers of the scanners interface to a remote location. System event data is transferred to the remote location by communicating with the web servers within the scanners. The data mining module monitors the system events in the scanners and records the system event data in log files. The log viewer component translates the log files to the web servers and the web servers transfer the system event data to the remote location at regular, pre-defined time intervals. The system event data is formatted such that the system event data may be displayed to an operator and/or provided to a customer for each scanner.

Certain embodiments of the present invention afford an approach to monitor and acquire system event data of multiple ultrasound scanners and transfer the data to a remotely located support center such that the monitoring/acquisition programs provide cross-platform/server interoperability and may be used on multi-generational products.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION

Figure 1:
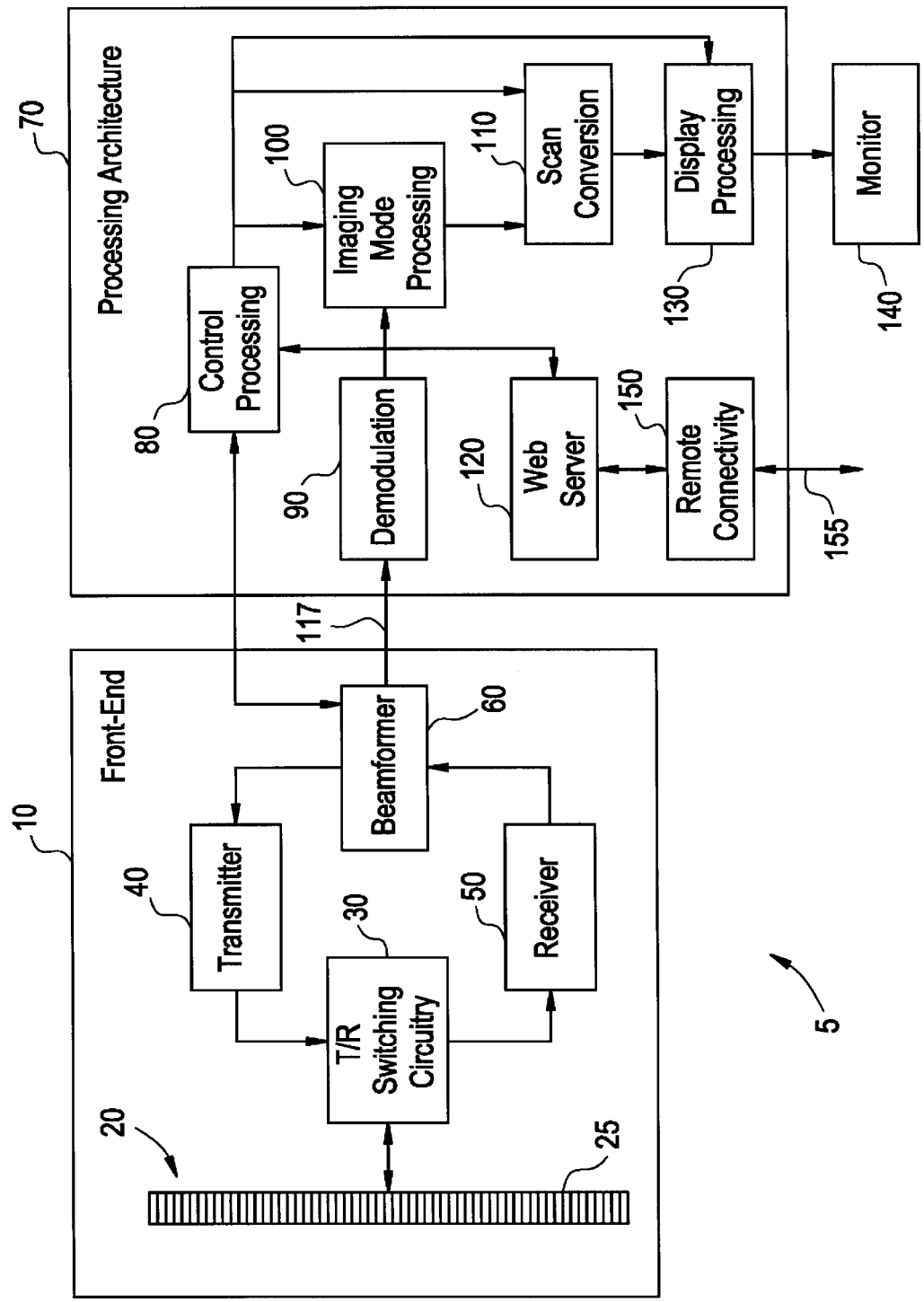
FIG. 1 is a schematic block diagram of a diagnostic ultrasound scanner formed in accordance with an embodiment of the present invention.

FIG. 1 is a schematic block diagram of an ultrasound system 5 in accordance with an embodiment of the present invention. The higher level illustrated elements of the ultrasound system 5 are the front-end 10 and the processing architecture 70. The front-end 10 comprises a transducer array 20 (comprising a plurality of transducer array elements 25), transmit/receive switching circuitry 30, a transmitter 40, a receiver 50, and a beamformer 60. Processing architecture 70 comprises a control processing module 80, a demodulation module 90, an imaging mode processing module 100, a scan conversion module 110, a display processing module 130, a web server 120, and a remote connectivity module 150. A monitor 140 is also provided.

The architectures and modules may be dedicated hardware elements such as circuit boards with digital signal processors or may be software running on a general purpose computer or processor such as a commercial, off-the-shelf PC. The various architectures and modules may be combined or separated according to various embodiments of the present invention.

In the front-end 10, the transducer array 20 is connected to the transmit/receive (T/R) switching circuitry 30. The T/R switching circuitry 30 is connected to the output of transmitter 40 and the input of receiver 50. The output of receiver 50 is input to beamformer 60. Beamformer 60 is further connected to the input of transmitter 40, to control processing module 80 and the input of demodulation module 90 in processing architecture 70 through digital interface 117.

In processing architecture 70, the output of demodulation module 90 is connected to an input of imaging mode processing module 100. Control processing module 80 interfaces to imaging mode processing module 100, scan conversion module 110, display processing module 130, and web server 120. An output of imaging mode processing module 100 is connected to an input of scan conversion module 110. An output of scan conversion module 110 is connected to an input of display processing module 130. Web server 120 is connected to remote connectivity module 150. The output of display processing module 130 is connected to the input of monitor 140. Remote connectivity module 150 provides the connection to an external network 250 (see FIG. 2) at connection 155.

The primary function of the ultrasound scanner 5 is to transmit ultrasound energy into a subject to be imaged, and receive and process backscattered ultrasound signals from the subject to create and display an image. To generate a transmitted beam of ultrasound energy, the control processing module 80 sends command data to the beamformer 60 which tells the beamformer to generate transmit parameters to create a beam of a certain shape that originates from a certain point at the surface of the transducer array 20 at a certain steering angle. The transmit parameters are sent from the beamformer 60 to the transmitter 40. The transmitter 40 uses the transmit parameters to properly encode transmit signals to be sent to the transducer array 20 through the T/R switching circuitry 30. The transmit signals are set at certain levels and phases with respect to each other and are provided to individual transducer elements 25 of the transducer array 20. The transmit signals excite the transducer elements 25 of the transducer array 20 to emit ultrasound waves with the same phase and level relationships. As a result, a transmitted beam of ultrasound energy is formed in a subject within a scan plane along a scan line when the transducer array 20 is acoustically coupled to the subject by using, for example, ultrasound gel. The process is known as electronic scanning.

The transducer array 20 is a two-way transducer. Once ultrasound waves are transmitted into a subject, the ultrasound waves are backscattered off of tissue and blood samples within the structure. The backscattered waves arrive at the transducer array 20 at different times, depending on the distance into the tissue they return from and the angle with respect to the surface of the transducer array 20 at which they return. The transducer elements 25 of the transducer array 20 are responsive to the backscattered waves and convert the ultrasound energy from the backscattered waves into received electrical signals.

The received electrical signals are routed through the T/R switching circuitry 30 to the receiver 50. The receiver 50 amplifies and digitizes the received signals and provides other functions such as gain compensation. The digitized received signals correspond to the backscattered waves received by each transducer element 25 at various times and preserve the amplitude and phase information of the backscattered waves.

The digitized received signals are sent to beamformer 60. The control processing module 80 sends command data to beamformer 60. Beamformer 60 uses the command data to form a receive beam originating from a point on the surface of transducer array 20 at a steering angle typically corresponding to the point and steering angle of the previous ultrasound beam transmitted along a scan line. The beamformer 60 operates on the appropriate received signals by performing time delaying and focusing, according to the instructions of the command data from the control processing module 80, to create received beam signals corresponding to sample volumes along a scan line in the scan plane within the subject. The phase, amplitude, and timing information of the received signals from the various transducer elements 25 is used to create the received beam signals.

The received beam signals are sent to processing architecture 70 over digital interface 117. Demodulation module 90 performs demodulation on the received beam signals to create pairs of I and Q demodulated data values corresponding to sample volumes within the scan plane. Demodulation is accomplished by comparing the phase and amplitude of the received beam signals to a reference frequency. The I and Q demodulated data values preserve the phase and amplitude information of the received signals.

The demodulated data is transferred to imaging mode processing module 100. Imaging mode processing module 100 uses parameter estimation techniques to generate imaging parameter values from the demodulated data in scan sequence format. The imaging parameters may comprise parameters corresponding to various possible imaging modes such as, for example, B-mode, color velocity mode, spectral Doppler mode, and tissue velocity imaging mode.

The imaging parameter values are passed to scan conversion module 110. Scan conversion module 110 processes the parameter data by performing a translation from scan sequence format to display format. The translation includes performing interpolation operations on the parameter data to create display pixel data in the display format.

The scan converted pixel data is sent to display processing module 130 to perform any final spatial or temporal filtering of the scan converted pixel data, to apply grayscale or color to the scan converted pixel data, and to convert the digital pixel data to analog data for display on monitor 140.

Figure 2:
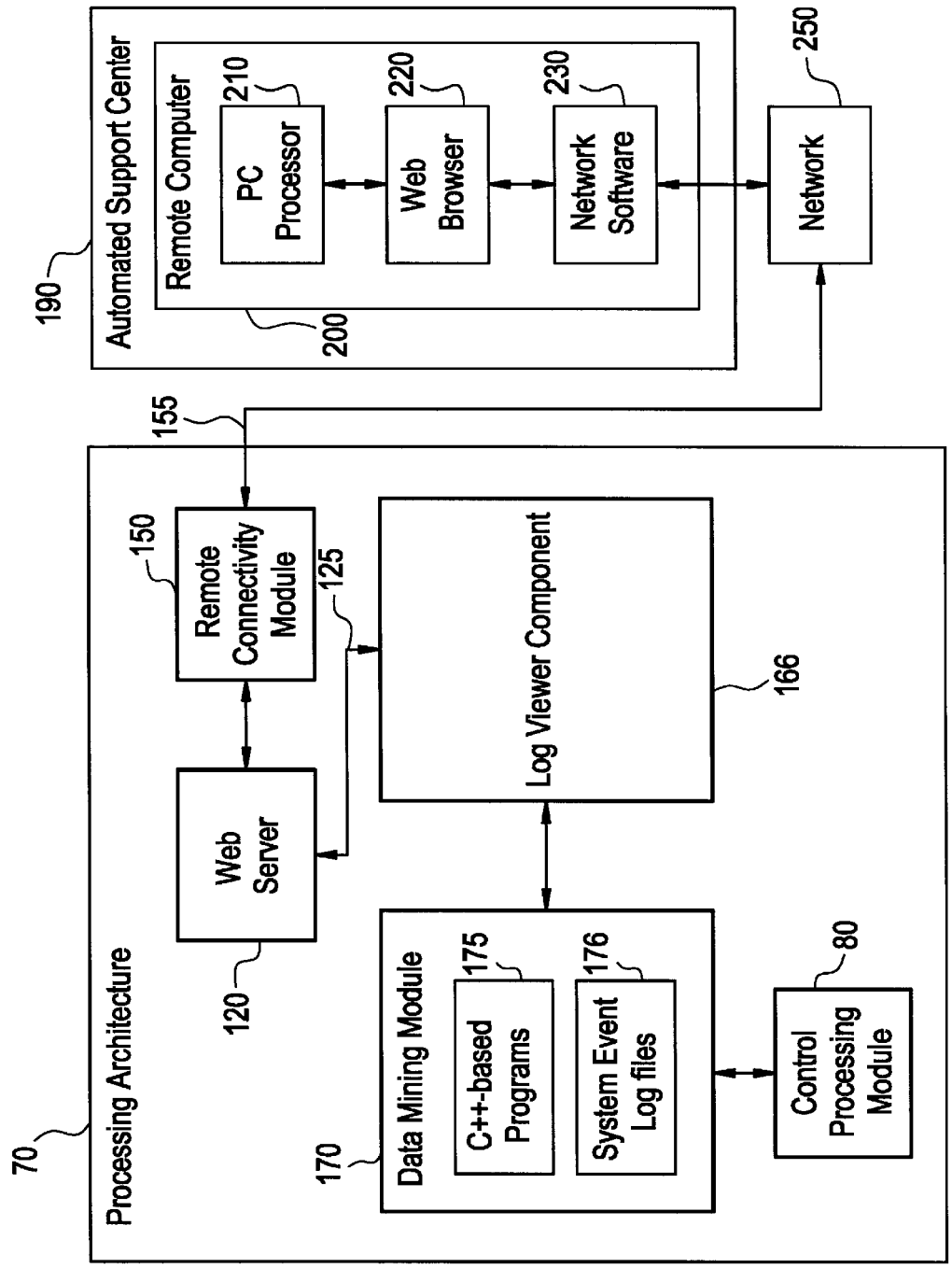
FIG. 2 is a schematic block diagram of a data mining configuration for the ultrasound scanner of FIG. 1, formed in accordance with an embodiment of the present invention, for monitoring and acquiring system event data from the scanner and formatting the system event data.

FIG. 2 is a schematic block diagram of a data mining configuration for an ultrasound scanner 5 used for monitoring and acquiring system events within the scanner 5 and transferring the system event data to a remote location from the scanner 5 in accordance with an embodiment of the present invention. The higher level elements of the data mining configuration illustrated comprise processing architecture 70, a network 250, and an automated support center 190.

FIG. 2 shows the data mining-related aspects of the processing architecture 70 comprising a Java-based log viewer component 166, a data mining module 170, a control processing module 80, a web server 120, and a remote connectivity module 150.

Within the processing architecture 70, web server 120 connects to remote connectivity module 150 and log viewer component 166. Log viewer component 166 connects to data mining module 170, and data mining module 170 connects to control processing module 80.

Automated support center 190 comprises at least one remote computer 200. Remote computer 200 comprises PC processor 210, web browser 220, and network software 230. Network 250 interfaces remote computer 200 to processing architecture 70 in ultrasound scanner 5.

The data mining module 170 comprises various C++-based monitoring programs 175 running on a computer and provide cross-platform interoperability. The Java-based log-viewer component 166 comprises a set of Java servlets running on a computer and a Java native interface to C and provide cross-platform/server interoperability. A Java servlet is a Java application that runs in a server-based environment and provides server-side processing, typically to access information or initiate processing. Java servlets and a native interface to C are supported on most platforms including unix based platforms and windows based platforms.

The web server 120 comprises a computer running standard server software so as to establish a standard HyperText Transport Protocol (HTTP) server within the scanner 5 that is able to connect to the Internet. The web server 120 may also comprise a set of HTML menus and Java applets to facilitate communication with a remote computer 200. A Java applet is a Java program that is downloaded from the server and run from the web browser. Java servlets and applets are more flexible than CGI scripts and are portable between platforms, servers, and operating systems.

In general, a web server provides WWW services on the Internet. A web server includes the hardware, operating system, web server software, TCP/IP protocols and web site content. The web server software refers to the HTTP server that manages web page requests from a browser and delivers HyperText Markup Language (HTML) documents (web pages) in response. The server also executes server-side scripts that provide functions such as data base searching.

HTTP is the communications protocol used to connect to web servers on the WWW. The primary function of HTTP is to establish a connection with a web server and transmit HTML pages to the client web browser.

The network 250 comprises the physical interface and software between the ultrasound scanner 5 and the remote computer 200. The network 250 may include telephone lines, routers and switchers, fiber optic cable, radio transmitters and receivers, or any other devices and software that may be used to establish a communications link between the ultrasound system 5 and remote computer 200. Typically, the network 250 comprises the Internet and the WWW. The web browser 220 is a program that serves as a front-end to the WWW on the Internet. The web browser 220 allows a user to view a site on the WWW.

The various architectures, components, modules, and interfaces within the scanner may be combined or separated according to various embodiments of the present invention. For example, the processing architecture 70 may comprise dedicated hardware elements such as circuit boards with digital signal processors or may be software running on a general purpose computer or processor such as a commercial, off-the-shelf PC. The log viewer component 166 and data mining module 170 may comprise software running on multiple dedicated computers or processors, or software running on a general purpose computer or processor such as a commercial, off-the-shelf PC.

The network 250 provides the communication link between the web server 120 within the scanner 5 and the remote computer 200 of the automated support center 190. Within the remote computer 200, a PC processor 210 employs a web browser module 220 and a network software module 230.

A system physically connects to a network through a port. An ultrasound scanner 5 may connect to a network 250 through, for example, a serial port. A modem is a device that converts information between the digital signals of a computer and the analog signals of telephone lines and vice-versa. Information from the web server 120 passes through the serial port on the digital side of the modem (i.e. between the server and modem). Communication with the modem is established by employing software that is known as a point-to-point (PPP) protocol. The PPP protocol is a standard protocol that allows multiple network protocols to be used over a serial connection such as a modem line. A network port and related functionality are provided by remote connectivity module 150.

Information is formatted and transferred across a network using software controlled communications protocols such as TCP/IP (Transmission Control Protocol/Internet Protocol). The IP protocol controls the routing of information through the network and the TCP protocol controls the actual transfer of information (packets) over the network.

An ultrasound scanner 5 may connect to a local network through, for example, an Ethernet connection. An Ethernet connection links the scanner to other scanners and systems on the local network. In a local Ethernet network, the systems on the network are within a certain allowable distance of each other and are connected through the same physical interface such as network wiring or fiber optic cable.

When information is to be sent from the ultrasound scanner 5 to a remote computer 200, the web server 120 employs the TCP/IP protocols to encapsulate the information into TCP packets. The TCP packets have header information that is used to track, check, and order the packets in the correct sequence for transmission. A given block of data comprises many packets and the packets may be routed differently over the Internet through different gateways. A gateway is a specialized computer used to connect and route packets of information between networks. The TCP protocol assures that the TCP packets are delivered to the correct destination in the correct order and without error.

Before transmission, the IP protocol is employed by the web server 120 to form IP packets from the TCP packets and having IP headers that provide addressing information that is used by the gateways to properly route the packets to their receiving destination. An IP header includes the Internet addresses of the source and destination. The IP protocol makes a best attempt to deliver all the packets but does not guarantee delivery.

At the receiving destination, (e.g. remote computer 200) the TCP packets are checked for errors according to the header information. Packets that are free of errors are acknowledged by the receiving destination and are placed in correct order to be reassembled into the original block of data. The transmitting source keeps track of packet acknowledgements. If a packet is not acknowledged in a certain amount of time, the packet is resent by the source (e.g. scanner 5). The receiving destination holds all received packets until all packets that make up the data block have been acknowledged. The packets are then correctly ordered and reassembled at the receiving destination.

TCP/IP is configured for the ultrasound scanner and the network environment to which the scanner is connected. For example, typical configuration information that is provided for TCP/IP comprises the user name and password associated with the scanner, the server address of the scanner, the IP address of the scanner, the type of local network the scanner may be connected to, and addresses of other scanners on the local network.

Every system connected to the Internet has a unique address. An IP address is a 32-bit address comprising four groups of 8 bits each separated by periods and specifying a connection to the Internet. A local network may use sub-network addressing such that each scanner on the local network has a sub-network address. The local network may be connected to the Internet as a single connection with a single IP address.

Domain name addressing is another type of addressing used in conjunction with the Internet where the user has a name associated with his network connection and the associated IP address number does not have to be directly known by the user. Domain name addressing is more convenient for the user since a meaningful domain name is preferable to a number.

The web server 120 in the scanner 5 is an HTTP server that interacts with the protocols (TCP/IP). The web server 120 is configured to communicate with a standard web browser 220 of a remote computer 200. The web server 120 provides pages of system event information to remote computer 200 at automated support center 190 at regular time intervals that are defined by the ultrasound scanner user or operator at the support center. The web server 120 interfaces with the Java-based log viewer component 166 to translate system event log files 176 in the data mining module 170.

The web server 120 is configured for such things as security by, for example, limiting access to certain users. Configuration information is stored in configuration files of the web server 120. Configuration files of the web server 120 may identify ports used by the web server 120 and, for example, the server administrator. The location of files used by the web server 120 are also included in the configuration files. The configuration files may also include the addresses of web pages and Java applets and servlets used by the web server 120.

At regular intervals, for example, once per day, the web server 120 transmits HyperText Markup Language (HTML) pages to the web browser 220. The HTML pages encapsulate the system event information sent to the remote computer 200. The information may include text, images, buttons, etc. HTML pages are easily created using standard software tools. The HTML pages are stored on the scanner 5 and the addresses of the HTML pages are configured in the web server 120. When it is time to send a specific system event web page of the scanner 5, the web server 120 finds the page and transmits its contents to the remote computer 200 over the network 250. The PC processor 210 executes the web browser module 220 to access the Internet through TCP/IP and PPP protocols configured for the remote computer 200. The remote computer 200 typically connects to the network 250 through a serial port and a modem in a similar manner as the scanner 5. The remote computer 200 used may be readily available commercially. Special hardware and software may not be required.

The log viewer component 166 includes a set of small executable programs called Java servlets that provide an interface between the web server 120 and the data mining module 170. Log viewer component 166 comprises a set of Java servlets to translate system event information in system event log files.

In an embodiment of the present invention, the data mining module 170 continuously monitors broadcasts, on a software bus, from a control processing module 80 in the scanner 5 for system events. The system events are converted into data points by data mining module 170 and captured in the form of system event log files 176. System event metrics may comprise number of scans performed over a certain time period, number of patients scanned over a certain time period, patient identification numbers, examination identification numbers, exam categories, current date of exam, exam start time, exam end time, active mode time, active exam probes, scanner product name, and calculations made during an exam.

At a pre-defined time, the log viewer component 166 translates a system event log file within the data mining module 170 of the scanner 5. The log viewer component 166 interprets and translates the system event data into an XML-based HTML page and the web server 120 transfers the HTML page over the network 250 to the remote computer 200 at automated support center 190. Again, the data mining module 170 and log viewer component 166 provide cross-platform/server interoperability and may be used on successive generations of ultrasound scanners and upgrades. CGI scripts, on the other hand, are specific to the platform and server and are not very portable to other platforms and operating systems.

The log viewer component 166 also in able to interpret various other log files stored on the ultrasound scanner and presents a productive analysis to a remote operator in response to requests. The log viewer component 166 translates log files from a text format to a XML-based HTML page. The HTML page is transferred to the web browser 220 in remote computer 200 and may be displayed per the style sheet defined for each log file. The method enables the various log files to have different presentations based on the information content. The log viewer component 166 also provides productivity-based functions including searching, analysis, and filtering which helps an operator to understand the recent usage of the scanner. For example, a user trying to understand recent abdominal probe usage for a scanner may filter a probe usage log file to locate the data points corresponding to abdominal probes used during a certain time period.

As a specific example, the automated support center is to receive probe usage data from scanner 5. At the appropriate time, log viewer component 166 interprets the appropriate system event log file and translates the system event data to an XML-based HTML format. The system event data is passed over the Internet by web server 120, using HTTP protocol, to remote computer 200. The system event data (being probe usage data in the example) is stored at automated support center 190 and may be viewed by an operator and/or formatted to be provided to a customer.

As a specific example of how system event data points are captured, a patient arrives in a scan room, an ultrasound operator selects the patient name from a patient list menu on the monitor 140 of ultrasound scanner 5. The control processing module 80 broadcasts a system event and the patient name is captured by the data mining module 170 and recorded in a log file. The ultrasound scanner 5 questions the operator whether to start a new exam or not. When the ultrasound operator selects the answer "yes" for the new exam from the menu, a system event is broadcast by control processing module 80 indicating that a new exam is starting. The data mining module 170 captures the new exam event and records the exam type and the time in a log file. The ultrasound operator continues to scan the patient, capturing and storing images. When the exam is complete, the ultrasound operator selects "end exam" and another system event is broadcast by control processing module 80 indicating that the current exam has ended. The data mining module 170 captures the event and records the time in the log file. As a result, the log file contains the starting and ending time for a particular exam performed on a particular patient.

The automated support center is able to communicate with multiple ultrasound scanners over the Internet where the multiple scanners are based on different platform architectures but employ the same type of common log viewer component and data mining module as described above which provide cross-platform/server interoperability. As an alternative, the system event data may be extracted from the log files and viewed by an ultrasound operator on the scanner monitor.

In summary, the advantages and features include, among others, the ability to monitor and record system event information and transfer the information over the Internet from a remote location by employing a Java-based log viewer component and a $C^{++}$-based data mining module within the scanner that provide cross-platform/server interoperability.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. Apparatus for acquiring system event data, at a third location, from ultrasound scanners being at locations remote from said third location, said apparatus comprising:
   a first ultrasound scanner being at a first location and being of a first platform type;
   a second ultrasound scanner being at a second location and being of a second platform type;

a first data mining module being at said first location and interfacing to said first ultrasound scanner to monitor first system events and capture first system event data in a set of first log files;

a second data mining module being at said second location and interfacing to said second ultrasound scanner to monitor second system events and capture second system event data in a set of second log files;

a first log viewer component being at said first location and interfacing to said first data mining module and translating said first system event data from said set of first log files to an Internet-compatible format at regular, pre-defined time intervals;

a second of log viewer component being at said second location and interfacing to said second data mining module and translating said second system event data from said set of second log files to an Internet-compatible format at regular, pre-defined time intervals;

a first web server cooperating with said first log viewer component at said first location to transfer said first system event data in said Internet-compatible format from said first location to said third location through an Internet protocol-based interface; and a second web server cooperating with said second instance of said log viewer component at said second location to transfer said second system event data in said Internet-compatible format from said second location to said third location through an Internet protocol-based interface.

2. The apparatus of claim 1 wherein said log viewer component comprises a common set of Java servlets and a common Java native interface to C providing cross-platform/server interoperability.

3. The apparatus of claim 1 wherein said data mining module comprises a common set of C++-based programs providing cross-platform interoperability.

4. The apparatus of claim 1 wherein said Internet-compatible format comprises an XML-based HTML page format.

5. The apparatus of claim 1 further comprising a network interfacing said first location and said second location to said third location wherein said network comprises the Internet.

6. The apparatus of claim 1 further comprising a remote computer at said third location and a network external to said first ultrasound scanner and said second ultrasound scanner and said remote computer, said remote computer having a web browser and communicating with said first ultrasound scanner and said second ultrasound scanner through said network.

7. The apparatus of claim 1 further comprising an automated support center at said third location to receive, process, and display said first system event data and said second system event data.

8. The apparatus of claim 1 further comprising a first remote connectivity module being at said first location and a network being external to said first ultrasound scanner, said first remote connectivity module interfacing said first web server to said network, and said remote connectivity module being based on Web technology.

9. The apparatus of claim 1 further comprising a second remote connectivity module being at said second location and a network being external to said second ultrasound scanner, said second remote connectivity module interfacing said second web server to said network, and said remote connectivity module being based on Web technology.

10. The apparatus of claim 1 wherein said Internet protocol-based interface comprises HTTP.

11. The apparatus of claim 1 wherein said first system event data is displayed at said third location and formatted such that said first system event data may be provided to a customer.

12. The apparatus of claim 1 wherein said second system event data is displayed at said third location and formatted such that said second system event data may be provided to a customer.

13. The apparatus of claim 1 wherein said first system event data and said second system event data comprise number of scans performed over a certain time period, number of patients scanned over a certain time period, patient identification numbers, examination identification numbers, exam categories, current date of exam, exam start time, exam end time, active mode time, active exam probes, scanner product name, and calculations made during exam.

14. A method for gathering and processing, at a third location, system event data in ultrasound scanners being at locations that are remote from said third location, said method comprising:

monitoring a first ultrasound scanner at a first location for first system events during normal operation of said first ultrasound scanner;

capturing first system event data associated with said first system events in a set of first log files at said first location;

translating said first system event data in said set of first log files to an Internet-compatible format at said first location in response to a first request from said first location;

transferring said first system event data in said Internet-compatible format to said third location in response to said first request;

monitoring a second ultrasound scanner at a second location for second system events during normal operation of said second ultrasound scanner;

capturing second system event data associated with said second system events in a set of second log files at said second location;

translating said second system event data in said set of second log files to an Internet-compatible format at said second location in response to a second request from said second location; and transferring said second system event data in said Internet-compatible format to said third location is response to said second request.

15. The method of claim 14 wherein said Internet-compatible format is an XML-based HTML page.

16. The method of claim 14 further comprising displaying said first system event data and said second system event data at said third location.

17. The method of claim 14 further comprising formatting said first system event data and said second system event data in a format that may be provided to a customer.

18. The method of claim 14 wherein said monitoring and capturing is performed by employing a common set of C++-based programs at said first location and said second location, said common set of C++-based programs providing cross-platform interoperabilty.

19. The method of claim 14 wherein said translating and transferring is performed by employing a common set of platform/server-independent, Java-based programs at said first location and said second location, said common set of Java-based programs comprising Java servlets and a Java native interface to C.

20. The method of claim 14 wherein said transferring employs an Internet protocol-based interface comprising HTTP.

21. The method of claim 14 wherein said third location comprises an automated support center to receive and process said first system event data and said second system event data.

22. The method of claim 14 wherein said first system event data and said second system event data comprises number of scans performed over a certain time period, number of patients scanned over a certain time period, patient identification numbers, examination identification numbers, exam categories, current date of exam, exam start time, exam end time, active mode time, active exam probes, scanner product name, and calculations made during exam.

23. A diagnostic ultrasound scanner comprising:
 a web server;
 a platform/server-independent log viewer component interfacing to said web server through an HTTP protocol interface;
 a data mining module interfacing to said log viewer component and providing cross/platform interoperability, said data mining module monitoring system events and capturing system event data; and
 a control processing module interfacing to said data mining module.

24. The ultrasound scanner of claim 23 further comprising a PC backend and a front-end, said PC backend interfacing to said front-end.

25. The ultrasound scanner of claim 23 further comprising a PC backend, said PC backend comprising an imaging mode processing module, a scan conversion module, said control processing module, and a display processing module.

26. The ultrasound scanner of claim 23 further comprising a remote connectivity module interfacing said web server to a network external to said ultrasound scanner.

27. The ultrasound scanner of claim 23 further comprising a monitor.

28. The ultrasound scanner of claim 21 wherein an automated support center, being at a location remote to said scanner, interfaces to said scanner through an Internet protocol-based network, said automated support center comprising a remote computer, and said remote computer comprising a PC processor, a web browser, network software, and a network connection.

29. The ultrasound scanner of claim 23 wherein an automated support center receives system event data over a network from said ultrasound scanner in response to an internal request from said scanner, and formats said system event data such that said system event data may be provided to a customer.

30. The ultrasound scanner of claim 23 wherein an automated support center receives system event data over a network from said ultrasound scanner in response to an internal request from said scanner, and displays said system event data at said automated support center.

31. The ultrasound scanner of claim 23 wherein said log viewer component comprises a set of Java servlets and a Java native interface to C, and said log viewer component is platform/server-independent.

32. The ultrasound scanner of claim 21 wherein said data mining module comprises a set of $C^{++}$-based programs, and said set of $C^{++}$-based programs providing cross-platform interoperability.

* * * * *